United States Patent [19]

Provost et al.

[11] Patent Number: 5,692,271

[45] Date of Patent: Dec. 2, 1997

[54] ENHANCED FLEXIBILITY FASTENER, METHOD AND APPARATUS FOR ITS MAKING, AND PRODUCT INCORPORATING IT

[75] Inventors: George A. Provost, Litchfield; James V. Stumpf, Goffstown, both of N.H.; A. Todd Leak, Neenah; Apiromraj S. Roslansky, Little Chute, both of Wis.

[73] Assignee: Velcro Industries B.V., Manchester, N.H.

[21] Appl. No.: 399,767

[22] Filed: Mar. 7, 1995

[51] Int. Cl.$^6$ .................................................. A44B 13/00
[52] U.S. Cl. ................................ 24/452; 24/442; 24/449
[58] Field of Search ........................... 24/452, 450, 449, 24/451, 442, 304, DIG. 11

[56] References Cited

U.S. PATENT DOCUMENTS

| | | | |
|---|---|---|---|
| 2,197,968 | 4/1940 | De Mattia . | |
| 3,086,529 | 4/1963 | Munz et al. . | |
| 3,113,803 | 12/1963 | Struble et al. | 24/450 |
| 3,134,152 | 5/1964 | Hsuen Ping | 24/449 |
| 3,141,461 | 7/1964 | Farris | 128/284 |
| 3,261,069 | 7/1966 | Mathison | 24/450 |
| 3,266,113 | 8/1966 | Flanagan, Jr. | 24/442 |
| 3,408,705 | 11/1968 | Kayser et al. | 24/452 |
| 3,423,764 | 1/1969 | Cassling | 2/337 |
| 3,967,622 | 7/1976 | Cepuritis | 128/287 |
| 4,144,887 | 3/1979 | Milnamow | 128/287 |
| 4,259,957 | 4/1981 | Sonenstein et al. | 128/287 |
| 4,470,794 | 9/1984 | Moertel . | |
| 4,894,060 | 1/1990 | Nestegard . | |
| 4,895,569 | 1/1990 | Wilson et al. | 604/386 |
| 5,067,210 | 11/1991 | Kayaki | 24/452 |
| 5,131,119 | 7/1992 | Murasaki et al. | 24/452 |
| 5,230,851 | 7/1993 | Thomas . | |
| 5,339,499 | 8/1994 | Kennedy et al. | 24/452 |

OTHER PUBLICATIONS

PCT Search Report PCT/US96/02970 Mar. 4, 1995.

*Primary Examiner*—Victor N. Sakran
*Attorney, Agent, or Firm*—Fish & Richardson P.C.

[57] ABSTRACT

An enhanced flexibility fastener product has a base and hook elements extending from the base. Rip-stops integrally molded with the base and with the hook elements are offset relative to the hook elements to reduce widthwise stiffness of the fastener product. The edge margins of the fastener are feathered in that they taper or otherwise reduce in thickness over an extended distance, preferably from at or near the hooks to the edge, resulting in a softer, less irritating fastener tape. Fasteners according to the invention are particularly advantageous on disposable absorbent garments such as diapers, sanitary napkins, and other articles of wear which come into contact with the user's skin.

21 Claims, 6 Drawing Sheets

ENHANCED FLEXIBILITY FASTENER, METHOD AND APPARATUS FOR ITS MAKING, AND PRODUCT INCORPORATING IT

BACKGROUND OF THE INVENTION

The invention relates to hook-and-loop fasteners, their manufacture, and products incorporating such fasteners.

Presently, it is known to use hook-and-loop fasteners on disposable absorbent garments, e.g., diapers and other similar garments, to secure the garment in place upon the body. Although the fasteners work quite well for their intended purpose, they tend to cause irritation to the flesh, especially when used next to babies' tender skin.

It is known to reduce the abrasiveness and tendency to scratch of hook tapes by reducing the stiffness, or flex modulus, of the polymer used to mold the tapes. In doing so, however, the hooks become ineffective because they, too, lose their stiffness and hence their ability to resist the forces required to hold a disposable absorbent garment in place.

Currently, the molded plastic hook fastener components used on disposable absorbent garments have a nominal base thickness of about 0.012 inches. The hooks are molded using a method like that disclosed in Fischer, U.S. Pat. No. 4,794,028, incorporated by reference, in which molten polymeric resin is introduced between a molding roller and a pressure-applying means which forces the resin into the hook-shaped cavities and allows for the formation of a base to which the hooks are integrally joined.

Because the base of the fastener component is quite thin, it is notch-sensitive. In other words, during use, the base is susceptible to tearing in the lengthwise direction, with the tear propagating between and parallel to the rows of hooks, when the base is notched or nicked by even slight tearing, or by sewing or otherwise securing the fastener to some other product.

To reduce this notch-sensitivity, so-called rip-stops have been integrally molded with the base of the fastener. These are typically of hump- or bump-form and lie in the spaces between rows of hooks. The rip-stops, which reduce notch-sensitivity by providing localized thickening of the base of the fastener, typically extend between and are integrally molded with the hooks in adjacent rows as well as the base.

For efficiency, the hook fastener components are produced in the form of wide intermediary tapes on the order of twelve to eighteen inches wide. These "wide-width tapes" have "selvedges" or blank spaces extending lengthwise along the tape at selected places across the width where eventual separation is desired. The selvedges are spaced apart by widths corresponding to the desired width of the final hook tape, e.g., half an inch to an inch with, for example, on the order of twenty to forty lengthwise rows of hooks between selvedges. The wide-width tape is subsequently split along the selvedges to separate it into individual hook tapes of the desired width. The individual hook tapes so produced will then have blank selvedge areas along either side that are half as wide as the selvedges running along the wide-width tape.

Splitting has been facilitated by molding splitting channels into the base of the fastener along the centers of the selvedges. As taught in Fischer, the molding roller is composed of an alternating stack of molding rings, which have hook-shaped cavities cut into their peripheries, and spacer rings. Unlike the spacer rings disclosed in Fischer which have flat peripheral edges, however, the spacer rings used when making hook tapes with rip-stops have hump-shaped indentations cut into their peripheries to form the rip-stops. The splitting channels are formed by splitting rings—a third type of ring incorporated into the stack of rings—that are thin and have a slightly larger diameter than the molding rings and spacer rings. The splitting rings have had rounded, "bullet-shaped" edges. These rings typically have been nominally on the order of 0.008 inches thick, with their overall diameter and the diameter of their edges selected such that the base of the fastener is reduced to the order of 0.002 inches thick at the bottom, center of the splitting channel.

A wide intermediary tape is split into the individual, final tapes by manually tearing the end of the wide-width tape a limited distance along each of the splitting channels to form leading ends of individual hook tapes, threading the leading ends through the fingers of a splitting comb, and pulling the tape past the fingers of the splitting comb. Because the splitting channel causes a localized weakness in the base of the fastener, the wide intermediary tape continues to split along the splitting channels as it is pulled continuously through the splitting comb. Alternatively, a splitting blade can be used instead of a splitting comb. The leading tape ends are alternately laced over the blade or under the blade and the wide intermediary tape is pulled past the blade, the blade continuously splitting it along the length of the splitting channels to produce the individual tapes.

Unfortunately, however, although this method of forming the individual narrow tapes is highly efficient, the edges of the individual tape have remained stiff and sharp and tend to produce the above noted skin irritation.

SUMMARY OF THE INVENTION

According to one important aspect of the invention, a molded plastic hook fastener product is provided for use in hook-and-loop fastening systems. The product comprises a base; a multiplicity of hook elements integrally molded with and rising from the base, the hook elements being arranged in rows extending lengthwise along a surface of the base and each of the hook elements defining a footprint on the surface where each the hook element joins the base; and a multiplicity of rip-stops integrally molded with and rising from the base, the rip-stops being arranged in rows extending lengthwise along the surface of the base and each of the rip-stops defining a footprint on the surface where each the rip-stop joins the base. According to the invention, the rows of rip-stops are interspersed among the rows of hook elements; at least many of the rip-stops are offset in the lengthwise direction relative to hook elements in widthwise adjacent rows such that a substantial lengthwise portion of the footprints of the respective offset rip-stops and adjacent hook elements do not overlap lengthwise; and the base has one or more feathered selvedge edges substantially devoid of hook elements.

Another aspect of the invention is the same product as described, but without selvedges or with selvedges of different form.

Preferred embodiments of these aspects of the invention have one or a number of the following features.

The rip-stops are hump-shaped.

For at least some of the rip-stops, most of the cross-sectional area of the rip-stop does not overlap lengthwise the cross-sectional areas of the one or two hook elements widthwise most adjacent to the rip-stop, the cross-sectional areas being taken in the lengthwise direction of the product.

For at least some of the rip-stops, lengthwise portions of the rip-stop footprints overlap lengthwise the footprints of the one or two hook elements widthwise most adjacent to the rip-stop. In a preferred form of this feature, the rip-stop is connected to the one or two hook elements widthwise most adjacent to the rip-stop.

For at least some of the rip-stops, lengthwise portions of the rip-stop footprint overlap lengthwise the footprints of two hook elements lengthwise adjacent to each other and lying in a row widthwise adjacent to the rip-stop. In a preferred form of this feature, the rip-stop is connected to one or both of the two hook elements lengthwise adjacent to each other, and preferably, equal lengthwise portions of the rip-stop footprint overlap lengthwise the footprints of the two hook elements lengthwise adjacent to each other.

According to another important aspect of the invention, a strip-form molded plastic product is provided. The product comprises a base; and the base has one or more feathered selvedge edges, devoid of functional structures or members, in which the thickness of the base decreases gradually, from a nominal value to a minimum value, over most of the width of the feathered selvedge edges.

Preferred embodiments of this aspect of the invention have one or a number of the following features.

The product is a hook fastener for use in hook-and-loop fastening systems, the product further comprising a multiplicity of hook elements integrally molded with and rising from the base, the hook elements being arranged in rows extending lengthwise along a surface of the base. More preferably, the product further comprises a multiplicity of rip-stops integrally molded with and rising from the base, the rip-stops being arranged in rows extending lengthwise along the surface of the base, the rows of rip-stops being interspersed among the rows of hook elements.

The thickness of the base decreases in the region of the feathered selvedge edges at an overall rate of less than or equal to about 0.5 in 1. Preferably, the thickness of the base decreases in the region of the feathered selvedge edges at an overall rate of between about 0.05 in 1 and about 0.5 in 1, and more preferably the thickness of the base decreases in the region of the feathered selvedge edges at an overall rate of about 0.05 in 1 or about 0.3 in 1.

In another important aspect, the invention provides a molded plastic product having enhanced conformability and skin comfort, the product comprising a base and a multiplicity of projections rising from the base, the projections disposed in a checkerboard fashion and being connected to each other at corners thereof so as to form a lattice of projections extending from the base, the base being of a nominal thickness between substantially all connecting projections.

In another important aspect, the invention provides an item of wear. The item of wear comprises a garment; and a molded plastic hook fastener for use in securing the garment on the body of a user of the garment. The fastener comprises a base; a multiplicity of hook elements integrally molded with and rising from the base, the hook elements being arranged in rows extending lengthwise along a surface of the base and each of the hook elements defining a footprint on the surface where each the hook element joins the base; and a multiplicity of rip-stops integrally molded with and rising from the base, the rip-stops being arranged in rows extending lengthwise along the surface of the base and each of the rip-stops defining a footprint on the surface where each the rip-stop joins the base, the rows of rip-stops being interspersed among the rows of hook elements; at least many of the rip-stops being offset in the lengthwise direction relative to hook elements in widthwise adjacent rows such that a substantial lengthwise portion of the footprints of the respective offset rip-stops and adjacent hook elements do not overlap lengthwise.

In another important aspect, the invention provides an item of wear comprising a garment; and a molded plastic hook fastener for use in securing the garment on the body of a user of the garment, the fastener comprising a base having one or more feathered selvedge edges, devoid of functional structures or members, in which the thickness of the base decreases gradually, from a nominal value to a minimum value, over most of the width of the feathered selvedge edges.

In preferred embodiments of either of these last two aspects of the invention, the item of wear is an article of sanitary wear, preferably a disposable absorbent garment.

In another aspect, an apparatus is provided for making molded plastic hook fasteners. The apparatus comprises a molding roller comprised of an alternating stack of molding rings and spacer rings, the molding rings having hook-forming cavities extending inward from peripheral surfaces thereof and the spacer rings having rip-stop-forming cavities extending inward from peripheral surfaces thereof. The molding rings and the spacer rings are disposed relative to each other such that the hook-forming cavities and the rip-stop-forming cavities are circumferentially offset relative to each other.

In another aspect, an apparatus is provided for forming a strip-form molded plastic item. The apparatus comprises a molding roller having radially enlarged, depression-forming enlargements, the diameter of the molding roller decreasing gradually on each side of the center of each enlargement, over most of the distance from the centers of the enlargements to the outer edges of the enlargements, from a maximum value at the centers of the enlargements to a nominal value at the edges of the enlargements.

In a preferred embodiment of this aspect of the invention, the strip-form molded plastic item is a hook fastener for use in hook and loop fastening systems, and the molding roller comprises an alternating stack of molding rings and spacer rings, the molding rings having hook-forming cavities extending inward from peripheral surfaces thereof. More preferably, the spacer rings have rip-stop-forming cavities extending inward from peripheral surfaces thereof.

BRIEF DESCRIPTION OF THE DRAWINGS

FIG. 7 is a schematic side view showing the respective orientation of hook-forming cavities and rip-stop-forming cavities used to make a fastener as shown in FIG. 3a.

DESCRIPTION OF PREFERRED EMBODIMENTS

Figure 1:
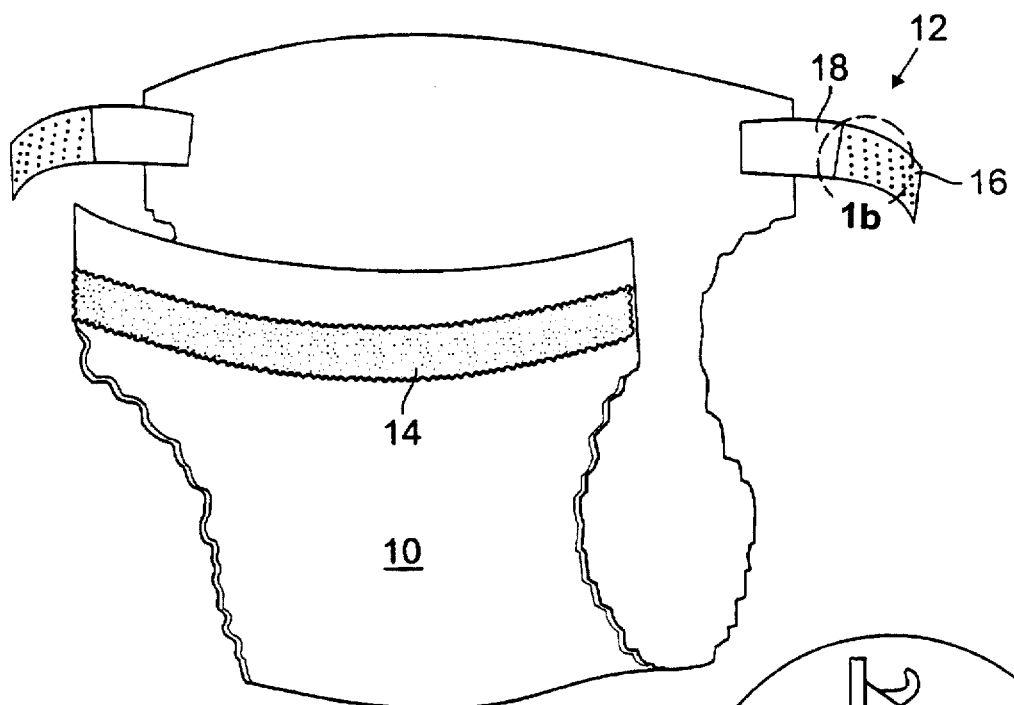
FIGS. 1 and 1a are perspective views showing, respectively, a disposable absorbent garment with an enhanced flexibility fastener and the garment in use.
Figure 1B:
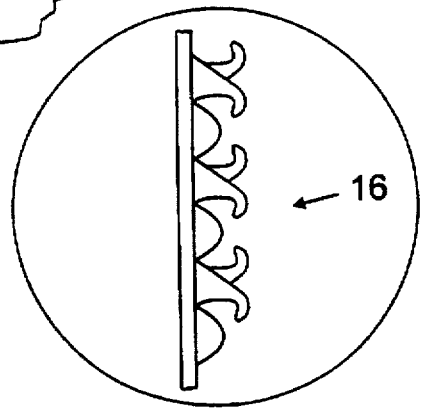
FIG. 1b is an enlarged view of area 1b in FIG. 1.
Figure 1A:
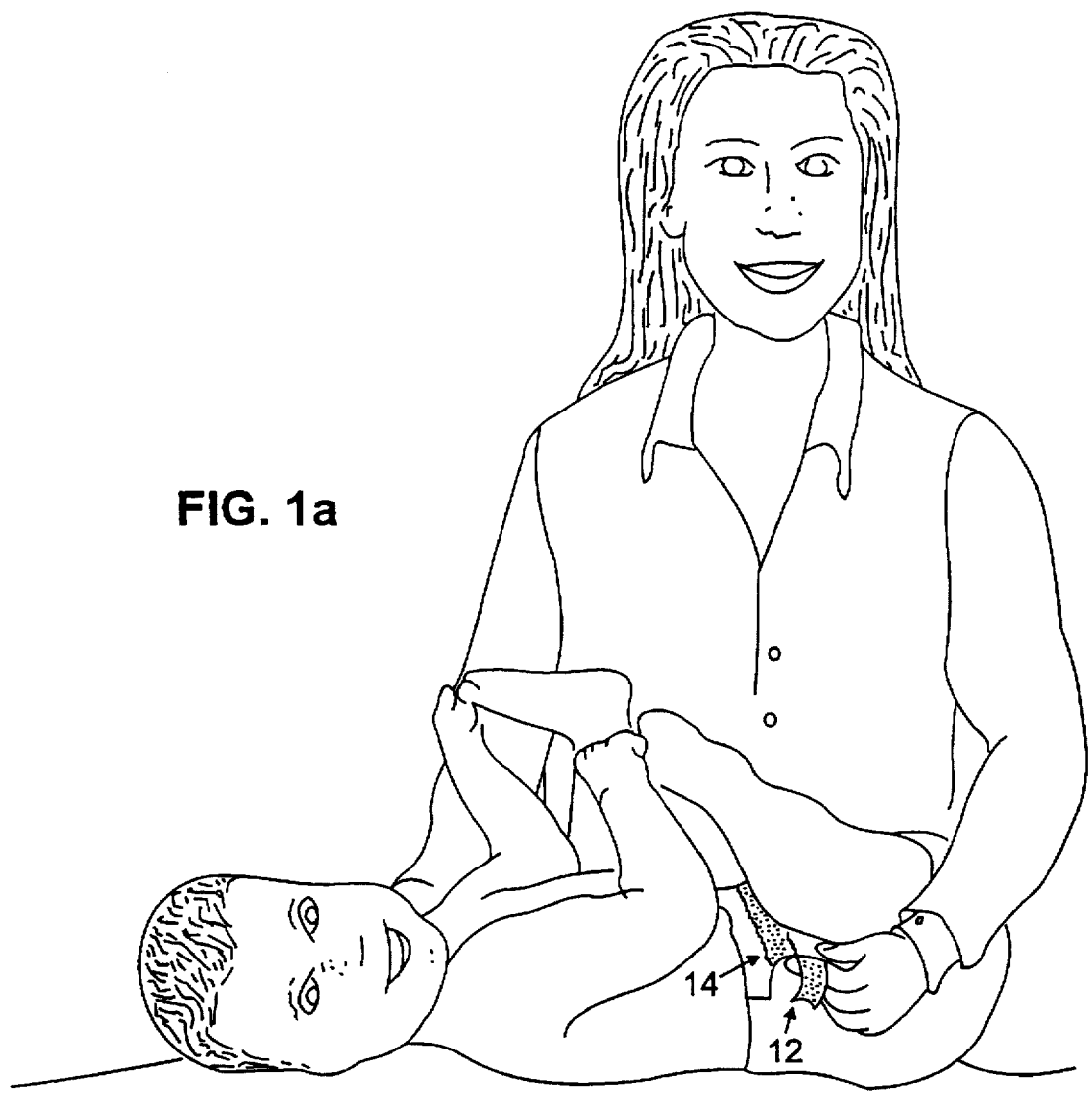

As shown in FIGS. 1 and 1b, a hook-and-loop fastenable disposable absorbent garment 10 has hook tabs 12 which mate with corresponding loop material 14 to secure the garment to a baby, as shown in FIG. 1a. The hook tabs 12 comprise a section 16 of molded plastic hook fastener tape, made according to the invention, which is attached to the garment 10 by way of a nonwoven strip 18, which may be made from the same material as the outer cover of the garment or some other material such as nonwoven laminates, film laminates, elastomerics, or other acceptable materials. Alternatively, the hook tape may be affixed directly to the body of the garment.

Figure 2:
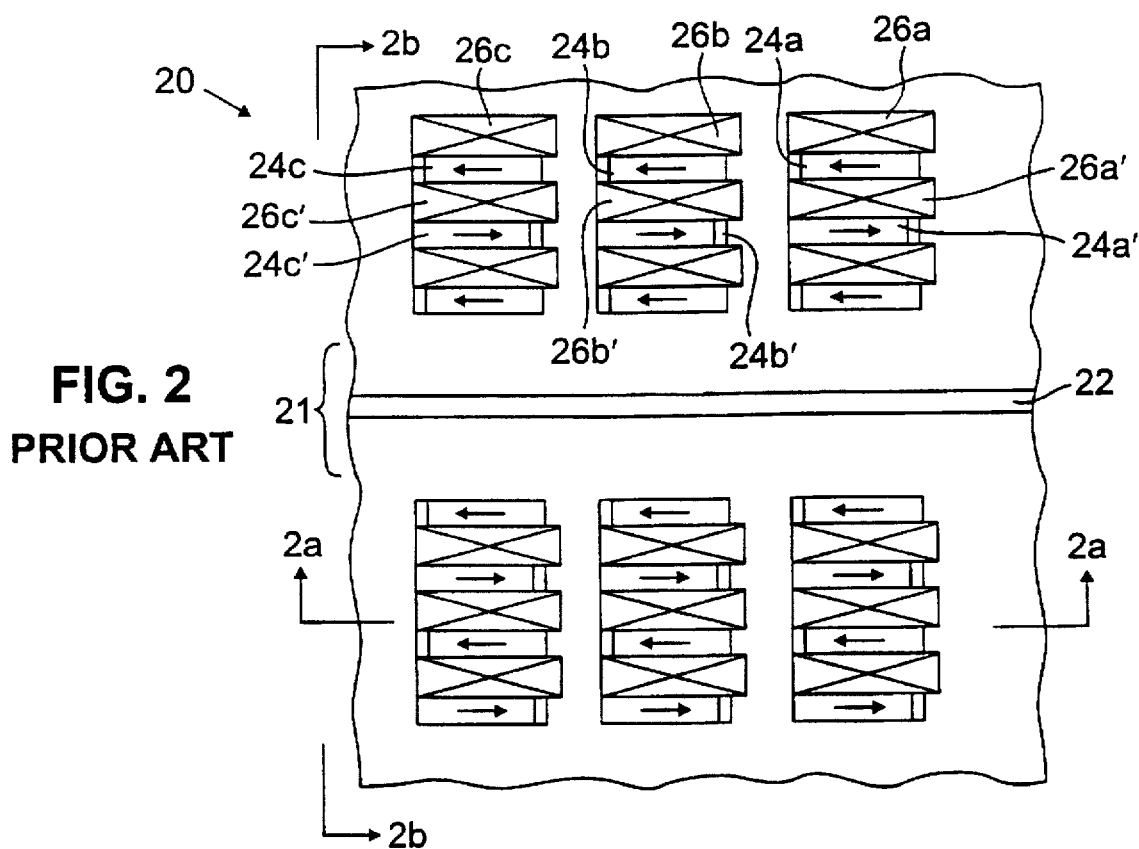
FIGS. 2, 2a, and 2b are plan, sectional side, and sectional end views, respectively, showing a prior art fastener with rip-stops and a splitting channel.
Figure 2A:
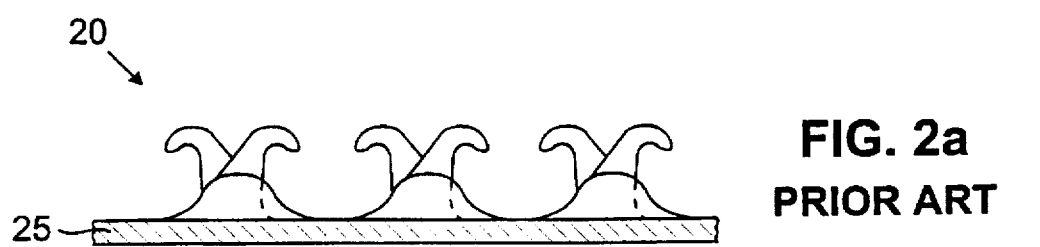
Figure 2B:
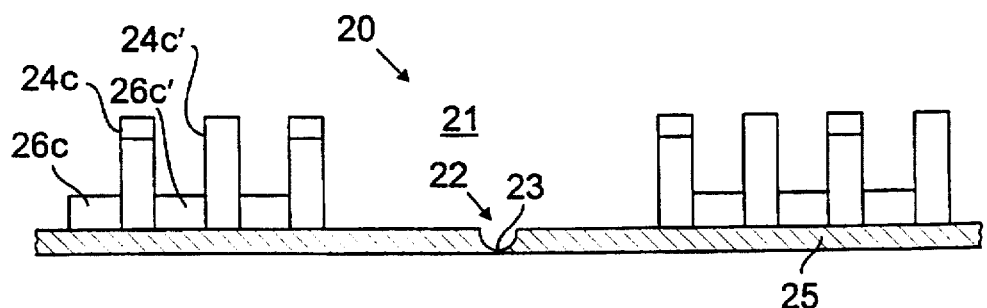

As shown in FIGS. 2, 2a, and 2b, a prior art rip-stop hook fastener tape 20 has rows of hooks, e.g. 24a, 24b, and 24c aligned in one lengthwise row and all facing the same direction, and hooks 24a', 24b', and 24c' aligned in a widthwise adjacent row and all facing the opposite direction. The direction in which each hook faces, i.e., the direction in which the top ends of the hooks face, is indicated by the arrows in FIG. 2. The hooks extend from and are integrally molded with the fastener base 25.

The prior art fastener tape also has hump-shaped rip-stops aligned lengthwise in rows, e.g. rip-stops 26a, 26b, and 26c are aligned in one row and rip-stops 26a', 26b', and 26c' are aligned in a widthwise adjacent row. The rip-stops, which are represented by the "X'ed" rectangles in FIG. 2, are integrally molded with the fastener base 25 as well as the two hooks between which each one is located.

As shown in FIGS. 2 and 2a in particular, the hooks and rip-stops are aligned across the width of the fastener tape, with widthwise adjacent hooks facing in alternating directions. It has been realized by the present inventors that because the hooks and rip-stops are all aligned in widthwise rows, they essentially form continuous ribs of plastic extending across the width of the fastener tape, and that these ribs contribute to a certain widthwise stiffness of the fastener tape.

As shown in FIGS. 2 and 2b, the hooks are grouped into sets of rows which are separated by selvedges 21, in which no hooks are formed, and narrow splitting channels 22 in the centers of the selvedges. The fastener base has a nominal thickness of about 0.012 inches, while the splitting channel is about 0.008 inches wide and the fastener base is about 0.002 inches thick at the bottom 23 of the splitting channel. It will be observed that the thickness of the fastener base remains constant throughout the selvedge area except for at the splitting channel. According to the invention, it is realized that because of such shape of the splitting channels, the selvedge areas bordering each of the individual, final fastener tapes are excessively and unnecessarily stiff.

Although only two sets of rows are shown in FIGS. 2 and 2b, with just a few rows of hooks and rip-stops in each set, it is to be understood that a wide intermediary hook tape will have several such sets of rows of hooks across the width of the tape, with on the order of twenty to forty rows of hooks and rip-stop in each set, and the intermediary tape is eventually separated into many narrower individual tapes by splitting it along the splitting channels. For example, a wide-width intermediary tape may be twelve to eighteen inches wide, with splitting channels spaced every half inch. Thus, when the intermediary tape is split, twenty-four to thirty-six individual hook tapes are produced, the exact number depending on the width of the intermediary tape and the spacing of the splitting channels. These dimensions, of course, are only exemplary and any desired width for the individual tapes or wide-width intermediary tape is considered to fall within the scope of the invention.

Figure 3:
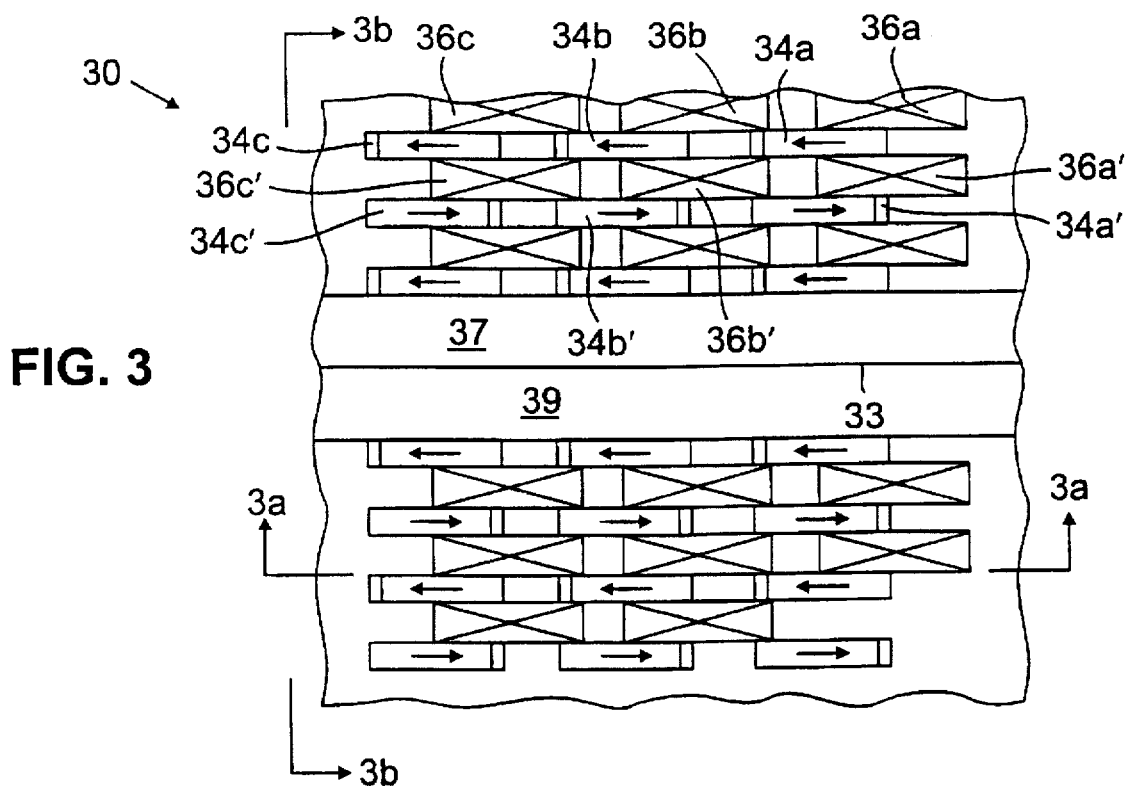
FIGS. 3, 3a, and 3b are plan, sectional side, and sectional end views, respectively, showing a fastener according to the invention in which the rip-stops have a special lengthwise-offset relationship relative to the hooks and in which a feathered splitting depression is provided.
Figure 3A:
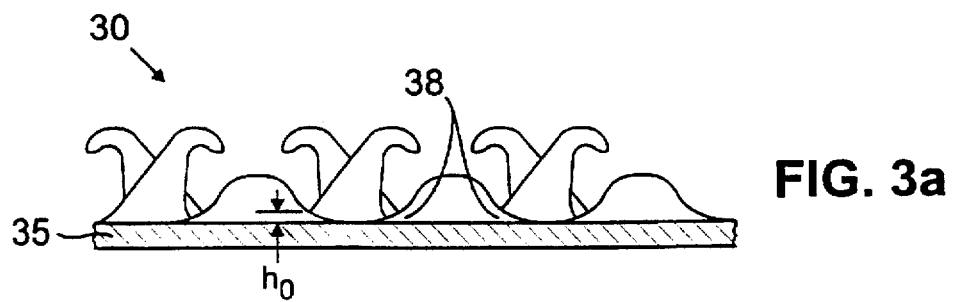
Figure 3B:
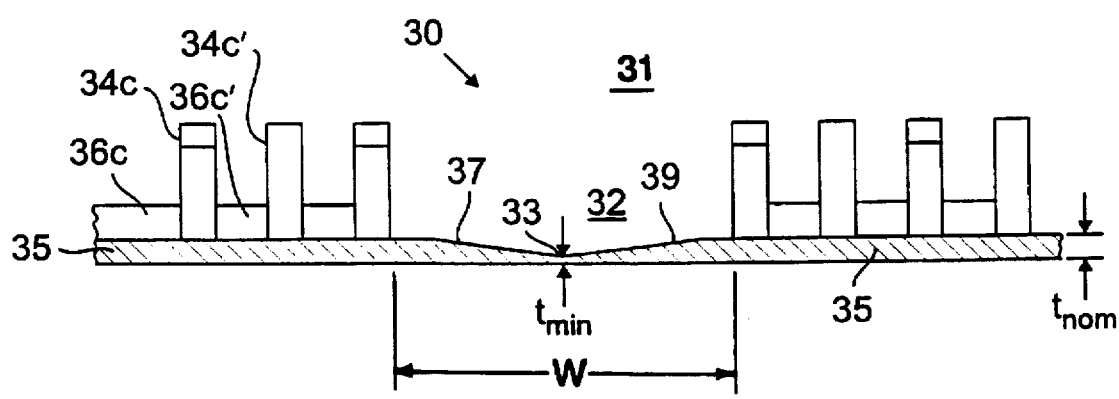

Referring to FIGS. 3, 3a, and 3b, a presently preferred embodiment of an improved fastener 30 according to the invention has rows of hooks, e.g. hooks 34a, 34b, and 34c arranged in one row and hooks 34a', 34b', and 34c' arranged in a widthwise adjacent row. The direction in which each hook faces, i.e., the direction in which the top, crook portion of the hooks faces, is indicated by the arrows in FIG. 3b. The hooks, which extend from and are integrally molded with the fastener base 35, may be of any desired profile, such as the one-way facing hook shape shown, a double-tipped palm tree-shape, or any other desired profile. It is presently preferred, for an inexpensive disposable garment product, to employ the hook shape and pattern shown.

The presently preferred embodiment of the fastener tape according to the invention also has hump-shaped rip-stops, e.g. 36a, 36b, and 36c aligned in one row and rip-stops 36a', 36b', and 36c' aligned in a widthwise adjacent row. The rip-stops, which are represented by the "X'ed" rectangles in FIG. 3, are integrally molded with the fastener base 35 and are located between adjacent rows of hooks.

Unlike the rip-stops in the prior art shown in FIGS. 2, 2a and 2b, the rip-stops of the present invention are longitudinally offset, or shifted, relative to the hooks. In other words, the "footprints" of the hooks and rip-stops, i.e., the regions of the surface of the base where each hook or rip-stop rises from the base, are shifted lengthwise so that they do not "overlap" substantially in terms of their lengthwise positioning such that the desired widthwise stiffness reduction is obtained.

Furthermore, although a symmetric profile is preferred for the rip-stops, e.g., the hump-shaped profile shown, it is possible that a non-symmetric profile could also be used. If some such non-symmetric profile is used, it is important that the majority of the cross-sectionally defined regions of the hooks and rip-stops do not overlap in the lengthwise direction, the cross-sections being taken along the lengthwise direction as shown in FIG. 3a.

Thus, whereas the rip-stops and hooks are all aligned in FIGS. 2, 2a and 2b, which has been found to make the fastener relatively stiff in the widthwise direction due to the continuous "rib" formed by the hooks and rip-stops (referred to collectively as "projections"), the discontinuous or checkerboard pattern in which the hooks and rip-stops are arranged in this preferred embodiment prevents the formation of such "ribs." As a result, a hook fastener according to the invention made with the same polymer and other general specifications is significantly more flexible and conformable than hook fasteners of the prior art.

With regard to the amount by which the rip-stops are offset relative to the hooks, although any amount of discontinuity or breakup of the alignment of the rip-stops and hooks that effectively reduces the widthwise stiffness of the fastener is within the scope of the invention, the offset pattern shown in FIG. 3 is presently preferred. In this configuration, the rip-stops are located such that they are evenly spaced between lengthwise adjacent hooks, and the fillets 38 at the bottoms of the rip-stops, where the rip-stops join the fastener base, slightly overlap in the lengthwise direction the fillets at the bottoms of the hooks (hidden behind the rip-stop fillets in FIG. 3a), where the hooks join the fastener base. The fillets of the rip-stops and hooks should overlap by an amount sufficient for the height of the overlapping portions, $h_o$, to retard tear propagation. This gives the product a checkerboard appearance, with a lattice of projections joined at their corners and between which the base of the fastener has its nominal thickness.

This configuration is found to maximize substantially stiffness reduction, but also maintains a degree of continuity across the width of the fastener tape of material that is thickened relative to the fastener base. This continuity of thickening contributes to maintaining the tear-preventing benefit of the rip-stops because tears in the fastener base tend to "find" and propagate through any gaps between the molded projections, and no such gaps are provided in this preferred embodiment.

FIGS. 3 and 3b also show, in combination with the rip-stop arrangement, another aspect of the invention that cooperates therewith to provide a particularly improved product. Unlike the hook fasteners of the prior art, as shown in FIGS. 2 and 2b, the wide intermediary hook tape created during the manufacture of a hook fastener according to the invention does not have a distinct, narrowly defined splitting channel in which the selvedge area, otherwise of constant thickness, thins down sharply to enable splitting. According to this aspect of the invention, the thickness of the fastener base 35 tapers over a significant portion of the width of the selvedge 31, from a nominal thickness $t_{nom}$ of about 0.012 inches at or near the sides of the hooks on either side of the selvedge to a minimum thickness $t_{min}$, on the order of about 0.002 inches, at the center 33 of the selvedge. This forms a gradually deepening depression 32, preferably maximized in the center of the region as shown, with the thickness of the base tapering down from its nominal value to its minimum value over half the width W of the selvedge.

In preferred embodiments useful for disposable absorbent garments, the width W is on the order of 0.065 inches. This results in an overall taper value, or rate of change of thickness, of approximately (0.012 inch–0.002 inch)÷(0.065 inch/2), or approximately 0.3 in 1. The actual taper value employed, however, may vary depending, e.g., on the nominal thickness of the tape or on the width of the selvedges extending along the intermediary tape which, in turn, is twice the width of the selvedges desired to border the final, individual fastener tapes. Taper rates that are more or less than 0.3 in 1 can, under certain circumstances, produce acceptable results for the intended purposes. Thus, taper values as low as 0.05 in 1 or as high as 0.5 in 1 are deemed to be within the scope of the invention.

Thus, the manner in which the base thickness changes throughout the selvedge may differ from that shown in FIG. 3. Although the splitting depression shown in FIG. 3 has a V-shaped profile such that the base thickness changes at a constant rate, with flat surfaces 37 and 39 forming the sides of the "V" and intersecting each other at the center 33 of the splitting depression, other profiles in which the base thickness changes non-linearly are also contemplated as falling within the scope of the invention. What is important for the broader aspects of the invention is that the base thickness changes gradually over the selvedge area, preferably from right at or near the hooks on either side of the selvedge to the center where the intermediary tape will be split. Stepwise reduction in thickness, or reduction at taper rates that vary over the width or alternate between tapering and non-tapering regions can also provide benefit under the broader aspects of the invention in gradually reducing the stiffness toward the edge of the fastener tape in a "feathering" manner. Such arrangements can result in final, individual fastener tapes that have soft, "feathered" selvedge edges that do not cause skin irritation the way prior art fasteners do.

Besides providing the desired feathered softness, splitting depressions 32 provided by gradual reduction in thickness are found to form sufficiently localized weaknesses in the base of the intermediary tape to enable precise splitting of the intermediary tape, yet provide sufficient integrity for handling purposes. The wide intermediary tape according to the invention is thus subsequently split into several narrow hook fastener tapes in the same way the prior art intermediary tape is: the end of the tape is manually torn along each of the splitting depressions to form a leading end; the leading ends are threaded through the fingers of a splitting comb or around a splitting blade; and the tape is pulled past the fingers of the splitting comb or the splitting blade to split it into the several narrower, final product tapes. Each final fastener tape product thus produced can have a soft, tapered edge on either side, each tapered edge being half of a selvedge area of the intermediary tape product.

Figure 4A:
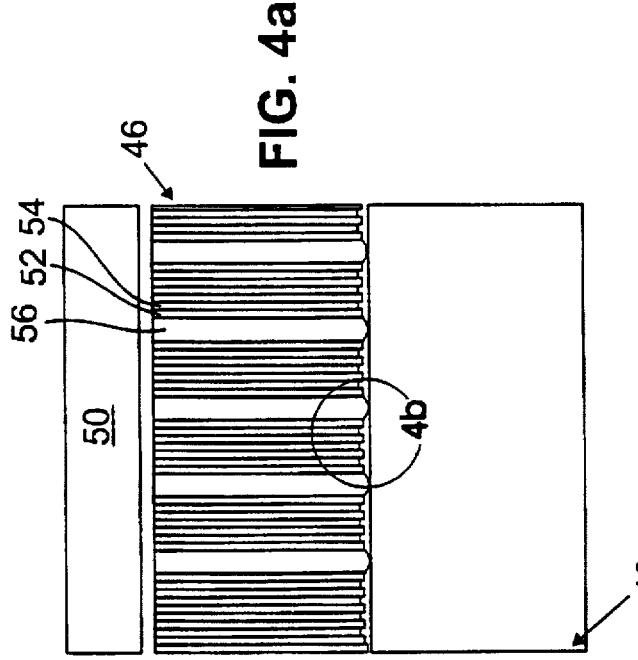
FIGS. 4 and 4a are schematic side elevational and end views, respectively, showing the apparatus and method used to make a fastener according to the invention.
Figure 4B:
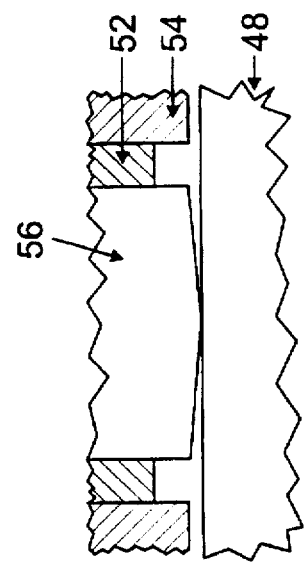
FIG. 4b is a close-up end view of the circled portion of FIG. 4a showing molding rings, spacer rings, and a depression ring used to make a preferred embodiment of a fastener according to the invention.
Figure 4:
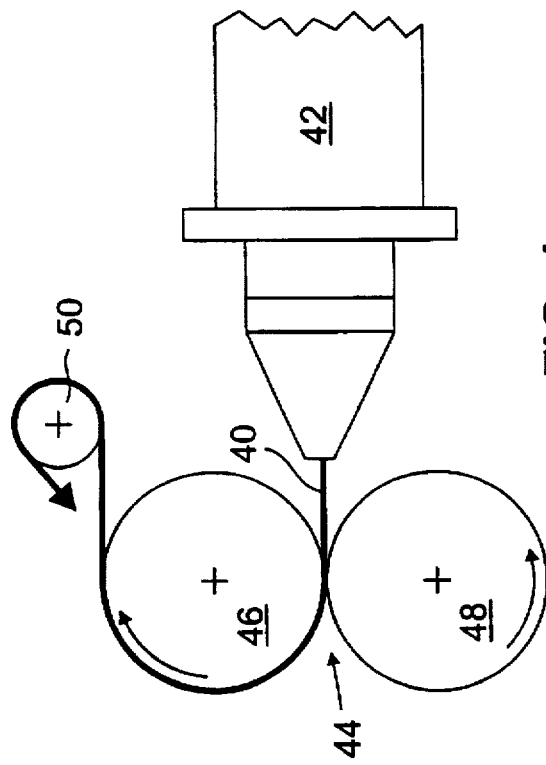
Figure 5:
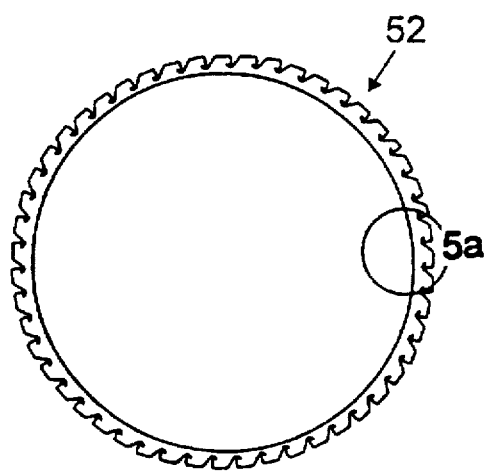
FIGS. 5 and 5a and FIGS. 6 and 6a are schematic side views, and close-up views of the circled portions thereof, showing the details, respectively, of a molding ring and a spacer ring used to make a preferred embodiment of a fastener according to the invention.
Figure 5A:
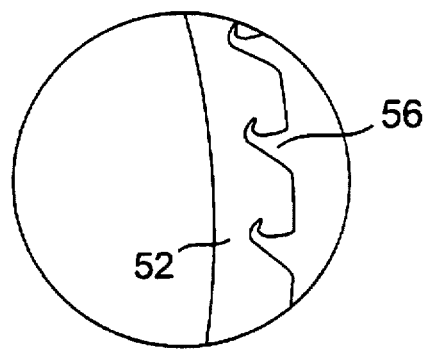
Figure 6:
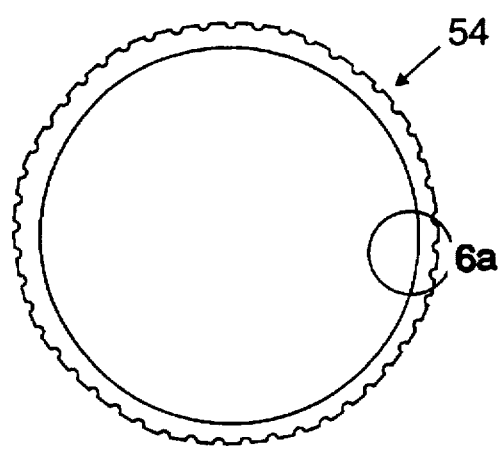
Figure 6A:
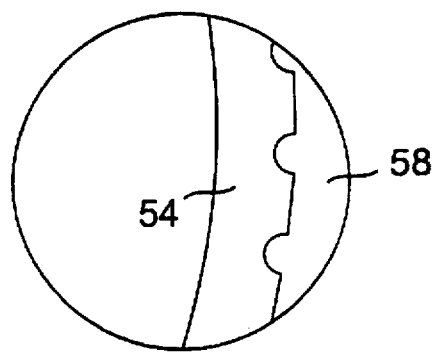

The method and apparatus used to make a fastener according to the invention are shown in FIGS. 4 through 7. As shown in FIG. 4, the product is preferably made by extruding molten plastic, i.e., polymeric resin, from an extruder 42 and directing it into the nip 44 formed between an internally cooled molding roller 46 and a pressure roller 48. Typical polymers include olefins—preferably polypropylene—polyesters, polyamides, or other thermoplastics. The pressure roller forces the resin into hook-shaped cavities located about the periphery of the molding roller, and the resin cools as it is carried on the surface of the rotating molding roller. After the resin has cooled sufficiently for the hooks to retain their shape, the intermediary fastener tape is pulled tangentially off of the molding roller by being passed around a take-off roller 50. In an alternative embodiment (not shown), the pressure-applying means may be constituted primarily by the extruder nozzle head, which is held in close proximity to the roll such as shown in Menzin et al., U.S. Pat. Nos. 3,752,619 and 3,758,657.

As shown in FIG. 4a and in greater detail in FIG. 4b, molding roller 46 is comprised of an alternating stack of molding rings 52 and spacer rings 54. Additionally, the molding roller comprises depression rings 56 spaced evenly throughout the stack by a dimension corresponding to the width of the final, narrow fastener tapes desired after splitting. Depression rings 56 are relatively wide, having a width corresponding to the width of the selvedges 31 that are to be formed in the intermediary hook tape (FIG. 3) and an edge profile that corresponds to the shape of the splitting depression 32 as shown in FIG. 3. In other words, the diameter of the depression ring decreases gradually, on both sides of the center of the ring, from the center of the ring to the edges of the ring.

Figure 7:
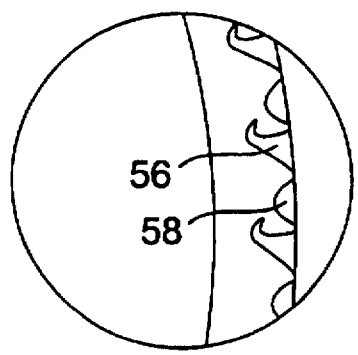

As shown in FIGS. 5, 5a, 6, and 6a, the molding rings have hook-shaped cavities 56 cut into their outer peripheral edges, and the spacer rings have hump-shaped, rip-stop-forming notches 58 cut into their outer peripheral edges. The molding rings and spacer rings are stacked onto and secured to the outer surface of a mandrel (not shown) with the hook-shaped cavities and the hump-shaped cavities in circumferentially offset relation to each other, as shown in FIG. 7. With this configuration, a wide intermediary hook tape as shown in FIGS. 3, 3a, and 3b is produced on the apparatus shown in FIGS. 4, 4a, and 4b. The intermediary hook tape is subsequently split, as discussed above, into several narrower hook tapes of the desired width with the desired feathered edges.

The final fastener product is significantly more flexible and softer to the touch than previously known molded plastic fastener products. The increased flexibility that results from the offset of the rip-stops increases the ability of the fastener tape to conform to the body shape and movements of a person wearing a disposable absorbent garment that utilizes a fastener according to the invention. The edges of the fastener are considerably softer and less likely to scratch than the edges of the prior art fastener tapes. The increased flexibility of the fastener tape also helps reduce scratching in that the tape will bend instead of pressing the edges or corners into the flesh. This is all accomplished in a hook tape that has structural integrity and that resists being torn or otherwise separated into pieces.

In certain other embodiments, each aspect of the invention alone can contribute desirable properties, although in combination they have a particularly effective, cooperative result on fasteners secured to or used in products having close proximity to the skin. An important product according to the inventor is a disposable absorbent garment, e.g., a diaper of the type shown in FIGS. 1 and 1a in which the hook fastener denoted at 16 is formed utilizing the various aspects of the invention.

Furthermore, it is contemplated that many other articles used close to exposed flesh are improved in combination with a fastener of the invention. For example, sanitary napkins are now available that use hook-and-loop fasteners to secure them in place; the comfort benefits of the enhanced flexibility of the present invention are clear. Adult incontinence garments may also make use of such fasteners, as may certain bandages and braces and other items which are likely to come into contact with the user's skin. Furthermore, the tapered edge aspect of the invention may be incorporated into other flexible strip-form products where enhanced user comfort is desired, or where it is desired that the flexibility of underlying parts not be impeded by the joining of a fastener tape thereto.

Other embodiments are within the scope of the following claims.

What is claimed is:

1. A molded plastic hook fastener product for use in hook-and-loop fastening systems, said product comprising:
   a base;
   a multiplicity of hook elements integrally molded with and rising from said base, said hook elements being arranged in rows extending lengthwise along a surface of said base and each of said hook elements defining a footprint on said surface where each said hook element joins said base; and
   a multiplicity of rip-stops integrally molded with and rising from said base, said rip-stops being arranged in rows extending lengthwise along said surface of said base and each of said rip-stops defining a footprint on said surface where each said rip-stop joins said base, said rows of rip-stops being interspersed among said rows of hook elements;
   at least many of said rip-stops being offset in the lengthwise direction relative to hook elements in widthwise adjacent rows such that a substantial lengthwise portion of the footprints of the respective offset rip-stops and adjacent hook elements do not overlap lengthwise;
   said base having one or more feathered selvedge edges substantially devoid of hook elements.

2. A molded plastic hook fastener product for use in hook-and-loop fastening systems, said product comprising:
   a base;
   a multiplicity of hook elements integrally molded with and rising from said base, said hook elements being arranged in rows extending lengthwise along a surface of said base and each of said hook elements defining a footprint on said surface where each said hook element joins said base; and
   a multiplicity of rip-stops integrally molded with and rising from said base, said rip-stops being arranged in rows extending lengthwise along said surface of said base and each of said rip-stops defining a footprint on said surface where each said rip-stop joins said base, said rows of rip-stops being interspersed among said rows of hook elements;
   at least many of said rip-stops being offset in the lengthwise direction relative to hook elements in widthwise adjacent rows such that a substantial lengthwise portion of the footprints of the respective offset rip-stops and adjacent hook elements do not overlap lengthwise.

3. The product of claim 1 or claim 2 wherein said rip-stops are hump-shaped.

4. The product of claim 1 or claim 2 wherein, for at least some of said rip-stops, most of the cross-sectional area of the rip-stop does not overlap lengthwise the cross-sectional areas of the one or two hook elements widthwise most adjacent to the rip-stop, said cross-sectional areas being taken in the lengthwise direction of the product.

5. The product of claim 1 or claim 2 wherein, for at least some of said rip-stops, lengthwise portions of the rip-stop footprints overlap lengthwise the footprints of the one or two hook elements widthwise most adjacent to the rip-stop.

6. The product of claim 5 wherein, for at least some of the rip-stops, the rip-stop is connected to the one or two hook elements widthwise most adjacent to the rip-stop.

7. The product of claim 1 or claim 2 wherein, for at least some of the rip-stops, lengthwise portions of the rip-stop footprint overlap lengthwise the footprints of two hook elements lengthwise adjacent to each other and lying in a row widthwise adjacent to said rip-stop.

8. The product of claim 7 wherein, for at least some of the rip-stops, the rip-stop is connected to one or both of the two hook elements lengthwise adjacent to each other.

9. The product of claim 7 wherein, for at least some of the rip-stops, equal lengthwise portions of the rip-stop footprint overlap lengthwise the footprints of the two hook elements lengthwise adjacent to each other.

10. The product of claim 9 wherein, for at least some of the rip-stops, the rip-stop is connected to one or both of said hook elements lengthwise adjacent to each other.

11. A strip-form molded plastic product formed in a running length, said product comprising
    a base, a broad surface of said base having fastener structures exposed for engagement with cooperating fastening structures to complete a fastening;
    the opposite broad surface of said base being exposed for face-to-face permanent attachment to a carrier sheet or strip,
    said base having at least one exposed longitudinal edge,
    said base having a feathered selvedge terminating at said edge, the thickness of said selvedge gradually decreasing toward said edge over most of the width of said selvedge, said selvedge being devoid of functional structures.

12. The product of claim 11 wherein said product is a hook fastener for use in hook-and-loop fastening systems, said product further comprising a multiplicity of hook elements integrally molded with and rising from said base, said hook elements being arranged in rows extending lengthwise along a surface of said base.

13. The product of claim 12, further comprising a multiplicity of rip-stops integrally molded with and rising from said base, said rip-stops being arranged in rows extending lengthwise along said surface of said base, said rows of rip-stops being interspersed among said rows of hook elements.

14. The product of claim 1 or claim 11 wherein the thickness of said base decreases in the region of said feathered selvedge edges at an overall rate of less than or equal to about 0.5 in 1.

15. The product of claim 14 wherein the thickness of said base decreases in the region of said feathered selvedge edges at an overall rate of between about 0.05 in 1 and about 0.5 in 1.

16. The product of claim 14 wherein the thickness of said base decreases in the region of said feathered selvedge edges at an overall rate of about 0.05 in 1.

17. The product of claim 14 wherein the thickness of said base decreases in the region of said feathered selvedge edges at an overall rate of about 0.3 in 1.

18. The product of claim 11 having enhanced conformability and skin comfort, said product further comprising a multiplicity of projections rising from said base, said projections disposed in a checkerboard fashion and being connected to each other at corners thereof so as to form a lattice of projections extending from said base, said base being of a nominal thickness between substantially all connecting projections.

19. The product of claim 11 in which said longitudinal edge is in a severed condition, having been previously joined during molding to the base of another such product.

20. The method of forming the strip-form molded plastic product of claim 19, comprising:

forming an intermediary tape comprising at least two such products integrally joined lengthwise in the region where the severed edges are to be formed, such that the thickness of the bases of the products gradually decreases, to a minimum value, toward the area where the severed edges are to be formed; and severing said tape along the region where the products are joined.

21. An intermediary tape formed during the manufacture of strip-form molded plastic products;

said intermediary tape comprising at least two product preforms, each preform comprising
a base,
a broad surface of said base having fastener structures exposed for engagement with cooperating fastening structures to complete a fastening,
the opposite broad surface of said base being shaped to be exposed for face-to-face attachment to a carrier sheet or strip,
said base having a feathered selvedge terminating at a region where a severed edge is to be formed, the thickness of said selvedge gradually decreasing toward said edge over most of the width of said selvedge,
said selvedge being devoid of functional structures;

said intermediary tape comprising at least two of said preform products integrally joined lengthwise in the region where the severed edges are to be formed, such that the thickness of the bases of the preforms gradually decreases, to a minimum value, toward the area where the severed edges are to be formed;

said products being separable to create said severed edges by tearing or cutting the tape lengthwise along the region where they are joined.

* * * * *